United States Patent
Hergeth

(10) Patent No.: US 6,888,083 B2
(45) Date of Patent: May 3, 2005

(54) APPARATUS AND METHOD FOR MONITORING COVER SHEET WEBS USED IN THE MANUFACTURE OF DIAPERS

(76) Inventor: Hubert A. Hergeth, Stesterstr. 4, Eynatten (BE), B-4731

( * ) Notice: Subject to any disclaimer, the term of this patent is extended or adjusted under 35 U.S.C. 154(b) by 350 days.

(21) Appl. No.: 10/118,654

(22) Filed: Apr. 8, 2002

(65) Prior Publication Data
US 2002/0162776 A1 Nov. 7, 2002

(30) Foreign Application Priority Data
Apr. 9, 2001 (DE) .......................... 101 17 699

(51) Int. Cl.⁷ .................................. B07C 5/00
(52) U.S. Cl. ................... 209/576; 209/577; 209/578; 156/64; 348/88; 382/141
(58) Field of Search ................. 209/576, 577, 209/939, 599

(56) References Cited

U.S. PATENT DOCUMENTS

| | | | |
|---|---|---|---|
| 4,837,715 A | * | 6/1989 | Ungpiyakul et al. .......... 702/82 |
| 5,045,135 A | * | 9/1991 | Meissner et al. ............ 156/64 |
| 5,068,799 A | * | 11/1991 | Jarrett, Jr. .................. 702/40 |
| 5,286,543 A | * | 2/1994 | Ungpiyakul et al. ..... 428/32.24 |
| 5,359,525 A | * | 10/1994 | Weyenberg ................ 700/124 |
| 5,659,538 A | * | 8/1997 | Stuebe et al. .............. 700/124 |
| 6,236,429 B1 | * | 5/2001 | Ho ............................. 348/88 |
| 6,404,910 B1 | * | 6/2002 | Ungpiyakul et al. ....... 382/141 |
| 6,565,686 B2 | * | 5/2003 | Bett et al. .................. 156/64 |

FOREIGN PATENT DOCUMENTS

| | | | |
|---|---|---|---|
| DE | 3729804 | 3/1989 | .......... G01N/21/89 |
| DE | 3921956 | 12/1990 | .......... G01B/11/06 |
| DE | 4304392 | 8/1994 | .......... G01N/21/89 |
| DE | 199 13 926 | 9/2000 | .......... D21F/7/00 |

\* cited by examiner

*Primary Examiner*—Donald P. Walsh
*Assistant Examiner*—Jonathan R Miller
(74) *Attorney, Agent, or Firm*—Darby & Darby

(57) ABSTRACT

An apparatus and method for detecting defects in the cover sheets used to manufacture diapers is disclosed. A linear sensor is used to detect defects in the cover sheet web before it is combined with the absorbent material to form a diaper. When a defect is detected, the manufactured diaper containing the defective cover sheet is ejected from the line after a delay which is dependent on the speed of the process.

8 Claims, 2 Drawing Sheets

APPARATUS AND METHOD FOR MONITORING COVER SHEET WEBS USED IN THE MANUFACTURE OF DIAPERS

This invention relates to an apparatus and method for detecting defects in cover sheets used in manufacturing diapers.

BACKGROUND OF THE INVENTION

Non-woven cover sheets are used in the manufacture of disposable diapers in order to cover the absorbent pads of cellular material.

These cover sheets must not contain any holes through which the cellular material might fall. They must also not contain thickened areas which interfere with the rapid incorporation of the cover sheets into the diaper during manufacture. Also, foreign matter on the cover sheet such as flies or dirt are obviously undesirable since it would be disturbing to customers.

During the manufacture of diapers, the cover sheet is supplied to the diaper making machine in the form of a continuous web. In the past, the cover sheet web has been monitored by a line camera with a lens. Such cameras are susceptible to soiling; they are also difficult to align and must be mounted at a significant distance from the web.

The main object of the present invention is to provide an improved method and apparatus for monitoring cover sheet webs used in the manufacture of diapers.

A more specific object of the invention is to provide an apparatus and method for monitoring cover sheet webs used in the manufacture of diapers which overcome the above-mentioned deficiencies of the known monitoring systems.

A further object of the invention is to provide a monitoring system of the type described wherein the resolution (number of available sensor points for a given width of the web) is greater than with current monitoring systems.

SUMMARY OF THE INVENTION

In accordance with the invention, a linear sensor is used to detect defects in cover sheet webs used in machines for manufacturing diapers. The sensor may be of the type used in scanners for personal computers and is arranged to scan the web prior to its incorporation into the diaper. When the sensor detects a defect in the diaper it generates a signal which is used, after a predetermined time delay, to eject the diaper containing the defective section of the cover sheet after it has passed through the diaper making machine.

DRAWINGS

DETAILED DESCRIPTION

Figure 1:
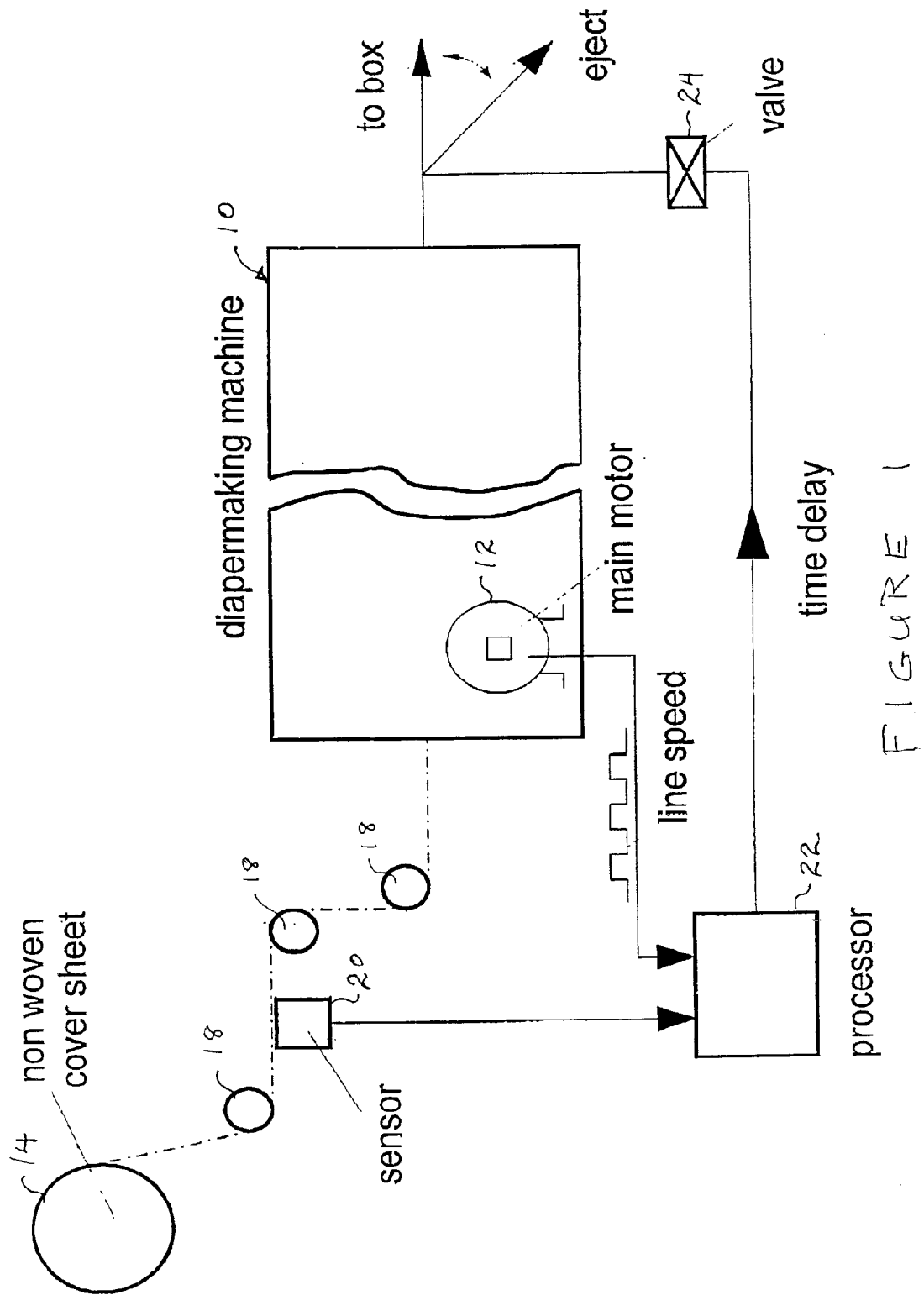
FIG. 1 is a schematic diagram of the invention.

FIG. 1 illustrates a diaper making machine at 10. The invention does not depend on a particular diaper making machine but, typically, such machines may be about sixty yards long and contain more than one hundred diapers in various stages of the manufacturing process. It is difficult to stop or interrupt the diaper making machine to eliminate a defective portion of the cover sheet and, in accordance with the invention, an entire diaper containing a cover sheet with a defective portion is eliminated after manufacture as explained below.

The diaper making machine includes a main motor 12 which drives the transport systems which move the diaper materials through the machine during the manufacturing process. The non-woven cover sheet is supplied in a roll 14 and is fed as a web by a series of rollers 18 into the machine 10 where it is joined with the absorbent material (not shown) to form diapers.

In accordance with the invention, a linear sensor 20 is provided near the point at which the cover sheet web 14 enters the machine 10. In the preferred embodiment, the sensor 20 is essentially the same as the sensor used in scanners designed for use with personal computers and extends across the entire width of web 14 (e.g. about 20 cm). When a defect occurs, it is sensed by the sensor 20 which then transmits a defect signal to processor 22. The processor 22 is also responsive to line speed signals which represent the line speed of the diaper making machine 10. The purpose of the line speed signals is to enable the system to determine precisely when a diaper manufactured with a defective cover sheet (as sensed by sensor 20) is exactly in position at an ejection gate so that it can be withdrawn from the line before packaging. Thus, after the processor 22 receives a defect signal from sensor 20, it counts the number of line speed pulses and, when the processor determines that the diaper manufactured with the defective cover sheet is at the ejector gate, it actuates a valve 24 to remove the defective diaper from the line.

The line speed pulses may be generated mechanically or electronically as long as they accurately represent the speed of the line so that if the line speed changes for any reason, the time delay provided by the processor before actuating the ejector gate is always the time required for the defective portion of the cover sheet to reach the ejector gate. The line speed pulses may be taken from the main motor or a driving shaft for the transport system, or they can be generated electronically, for example, by the computer control for the machine. Ejection is always triggered after a predetermined number of pulses which ensures that ejection occurs precisely as the diaper with the defective cover sheet reaches the ejection gate.

Figure 2:
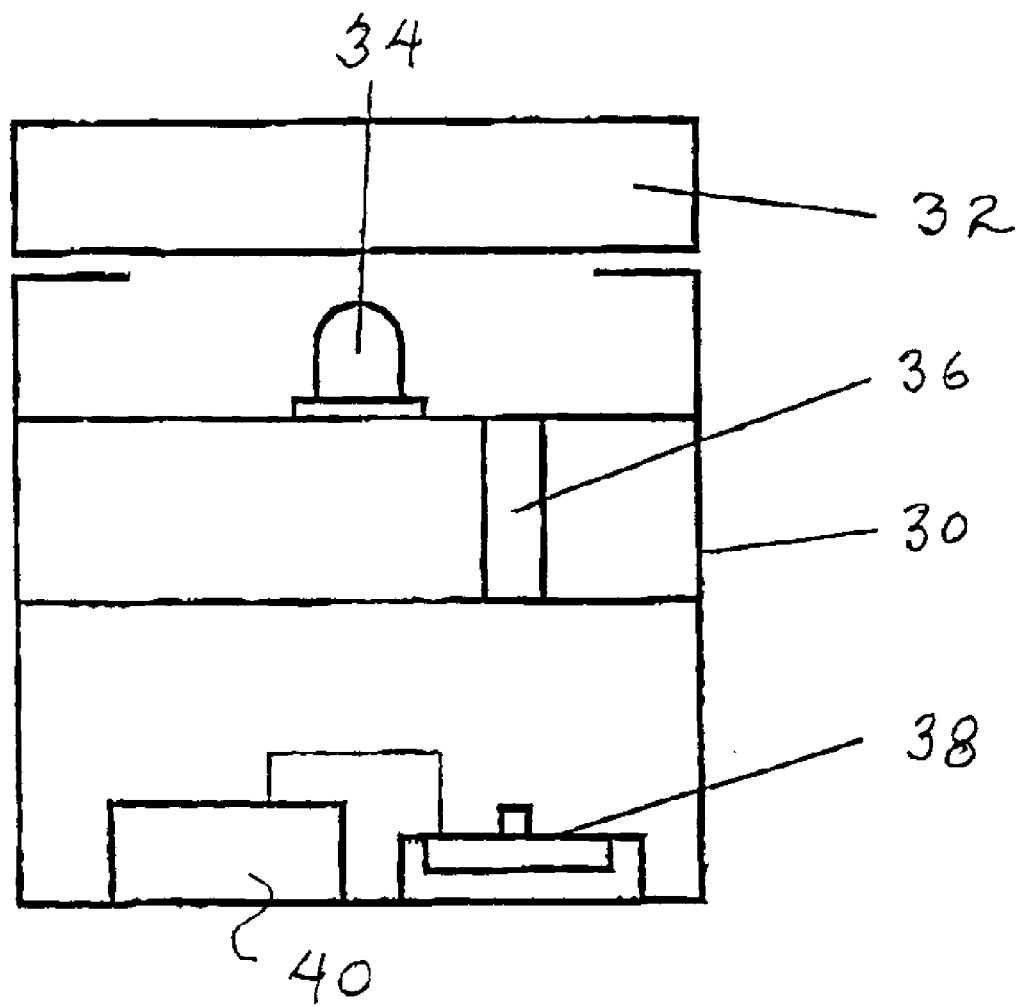
FIG. 2 is a diagrammatic illustration of a linear sensor that can be used in accordance with the invention.

The invention does not require a specific sensor but, in the preferred embodiment, a linear sensor of the type used in scanners for personal computers is preferred. FIG. 2 illustrates diagrammatically the construction of such a scanner.

The scanner includes a housing 30 which may be an aluminum extrusion. The housing is open at its top and covered by a glass plate 32 which includes a non-reflective coating. A line of LED's 34 is supported within the housing although other light sources may be used as well. The sensor is arranged so that the cover sheet web 14 passes over the glass plate 32. Light from the LED's is reflected from the cover sheet through a lens 36 onto an array of photosensitive elements 38. The photosensitive elements 38 are preferably CMOS elements lined up on a plastic sheet with a density of about 8,000 pixels per meter. If desired, several sensor lines of different colors can be provided.

The signals from the photosensitive elements 38 are preprocessed in an analog-to-digital converter 40. The output of converter 40 is the defect signal which is passed to the processor 22 of FIG. 1. The entire unit can be sealed with only the wires for the power supply and defect signals leaving the housing. Because the cover sheet web is guided directly over the glass plate 32, the sensor unit which is compact and easy to handle, is also dust resistant.

What is claimed is:

1. A method for detecting defects in a web used in the manufacture of diapers, comprising the steps of:

feeding the web to a diaper making machine which combines the web with an absorbent material to produce a diaper, using a linear sensor to detect defects in the web before it is combined with the absorbent material, and using a signal generated by the sensor indicative of a defect in the web to eject the diaper produced by the diaper making machine which contains the defect in the web.

2. A method according to claim 1, wherein the linear sensor extends over an entire width of the web.

3. A method according to claim 1, wherein a plurality of linear sensors are used to detect said defects, the linear sensors being responsive to different colors.

4. A method according to claim 1, wherein a line speed signal which represents the speed of the manufacturing process causes the diaper containing the defect in the web to be ejected.

5. Apparatus for detecting defects in a web material used in the manufacture of diapers, comprising:

means for feeding the web to a diaper making machine which combines the web with an absorbent material to produce a diaper, a linear sensor for detecting defects in the web before it is combined with the absorbent material, and means responsive to a signal generated by the sensor indicative of a defect in the web for ejecting the diaper produced by the diaper making machine which contains the defect in the web.

6. Apparatus according to claim 5, wherein the linear sensor extends over an entire width of the web.

7. Apparatus according to claim 5, wherein a plurality of linear sensors are used to detect said defects, the linear sensors being responsive to different colors.

8. Apparatus according to claim 5, including means for generating a line speed signal depending on the speed of the manufacturing process, said ejecting means being responsive to said line speed signal.

* * * * *